US009886965B1

(12) United States Patent
Ahmet et al.

(10) Patent No.: US 9,886,965 B1
(45) Date of Patent: Feb. 6, 2018

(54) SYSTEMS AND METHODS FOR PSYCHOACOUSTIC PROCESSING OF AUDIO MATERIAL

(71) Applicants: Zappa Ahmet, Sherman Oaks, CA (US); Finbar O'Hanlon, Port Melbourne (AU)

(72) Inventors: Zappa Ahmet, Sherman Oaks, CA (US); Finbar O'Hanlon, Port Melbourne (AU)

( * ) Notice: Subject to any disclaimer, the term of this patent is extended or adjusted under 35 U.S.C. 154(b) by 0 days.

(21) Appl. No.: 15/255,109

(22) Filed: Sep. 1, 2016

Related U.S. Application Data

(60) Provisional application No. 62/212,599, filed on Sep. 1, 2015.

(51) Int. Cl.
*G10L 21/013* (2013.01)
*H04R 3/04* (2006.01)
*G10H 1/00* (2006.01)

(52) U.S. Cl.
CPC ......... *G10L 21/013* (2013.01); *G10H 1/0008* (2013.01); *H04R 3/04* (2013.01); *G10H 2210/325* (2013.01)

(58) Field of Classification Search
None
See application file for complete search history.

(56) References Cited

U.S. PATENT DOCUMENTS

| | | | | |
|---|---|---|---|---|
| 5,892,833 A * | 4/1999 | Maag | ........................ | H04R 3/04 381/103 |
| 6,868,377 B1 * | 3/2005 | Laroche | .................. | G10L 19/20 341/111 |
| 8,964,993 B2 * | 2/2015 | Fairey | ...................... | H04R 5/04 381/17 |
| 9,609,451 B2 * | 3/2017 | Noh | ........................ | H03G 5/005 |
| 2009/0060209 A1 * | 3/2009 | Takeishi | .................... | H04R 3/04 381/17 |
| 2012/0140951 A1 * | 6/2012 | Solbach | .............. | G10L 19/0204 381/94.3 |
| 2014/0372107 A1 * | 12/2014 | Vilermo | ................ | G10L 19/265 704/205 |

* cited by examiner

*Primary Examiner* — Paul Huber
(74) *Attorney, Agent, or Firm* — Richard E. Ballard

(57) ABSTRACT

Systems and methods herein utilize psychoacoustic principles to process audio signals to achieve a desired result. In some embodiments, an exemplary process utilizes a combination of re-harmonization and auditory processing techniques in which a plurality of filtered audio cues are sampled, created and down-mixed into a final music file output, which may be designed to trigger specific effects on the function of the body and the brain. In some embodiments, enhanced audio material may be altered during the stream or fixed for a desired result at the beginning of the stream. In some embodiments, a signal enhancement process may be embedded into silicon or a media player, decoder or device with software. In other embodiments, audio or video material may be encoded or finalized into the media file.

20 Claims, 6 Drawing Sheets

SYSTEMS AND METHODS FOR PSYCHOACOUSTIC PROCESSING OF AUDIO MATERIAL

CROSS REFERENCE TO RELATED APPLICATIONS

This application claims benefit of U.S. Provisional Application Ser. No. 62/212,599, filed Sep. 1, 2015 and titled "Systems and Methods for Psychoacoustic Processing of Audio Material", which application is incorporated by reference herein in its entirety.

TECHNICAL FIELD

The disclosed embodiments relate generally to signal processing and in particular to systems and methods for providing enhanced audio material.

BACKGROUND

Unless otherwise indicated herein, the approaches described in this section are not prior art to the claims in this application and are not admitted to be prior art by inclusion in this section.

Psychoacoustics is the scientific study of sound perception. More specifically, it is the branch of science studying the psychological and physiological responses associated with sound (including speech and music).

Hearing is not a purely mechanical phenomenon of wave propagation, but is also a sensory and perceptual event. In other words, when a person hears something, that something arrives at the ear as a mechanical sound wave traveling through the air; but within the ear it is transformed into neural action potentials. These nerve pulses then travel to the brain where they are perceived. Hence, in many problems in acoustics, such as for audio processing, it may be advantageous to take into account not just the mechanics of the environment, but also the fact that both the ear and the brain are involved in a person's listening experience.

There remains a need for improved systems and methods for processing audio signals to achieve desired psychoacoustic properties.

SUMMARY

Described herein are systems and methods for psychoacoustic processing of audio materials. In some embodiments, a psychoacoustic process for acoustically enhancing audio material provides a more engaging listener experience by creating specific physical stimuli. In some embodiments, a process for providing enhanced audio material includes a combination of re-harmonization and auditory processing techniques, wherein a plurality of filtered audio cues are sampled, created and down-mixed into a final music file output, which is designed to trigger specific effects on the function of the body and the brain.

In some embodiments, a process for providing enhanced audio material (sometimes referred to herein as "Rezonyx") integrates new methods and processes with proven existing psychoacoustic principles to create the desired material. In some embodiments, harmonic data is altered to provide a desired result, but the timbre, dynamics and integral sound qualities of the original material is preserved. Such processes may be applied to prerecorded or live audio material via software or hardware, for example.

In some embodiments, a Rezonyx process has been configured in order to improve the experience of audio engagement, and may be designed for any audience where the importance of the audio material is paramount to the value of the content.

In some embodiments, by introducing a harmonically layered combination of frequencies and binaural beats to existing audio material, the brain can be induced into states of focused concentration, deep relaxation, intense creativity, and more, while stimulating various parts of your brain to work together in synchronization. By stimulating the brain to produce or decrease certain brainwave bands, a variety of mental states and emotional reactions, including meditation, excitation, motivation, anxiety, irritation, sexual excitement, relaxation, and spiritualism, can be achieved.

In some embodiments, the result of embedding Alpha waves into music listening provides a very relaxing experience for the listener.

In some embodiments, polyphonic retuning may be used to retune a variety of instruments, e.g., away from the standard of 12-tone temperament scaling and A 440 base reference to an optimal frequency for each note in the scale. By recalibrating the frequencies of sound using systems and methods described herein, notes within the music and other audio material may resonate better with the human physiology. Such new processes of tuning instruments may provide musicians and artists with a new way to create music that provides a more engaging experience.

These as well as other aspects and advantages will become apparent to those of ordinary skill in the art by reading the following detailed description, with reference where appropriate to the accompanying drawings. Further, it should be understood that the embodiments described in this overview and elsewhere are intended to be examples only and do not necessarily limit the scope of the invention.

BRIEF DESCRIPTION OF THE DRAWINGS

Example embodiments are described herein with reference to the drawings.

Like reference numerals refer to the same or similar components throughout the several views of the drawings.

DESCRIPTION OF EMBODIMENTS

I. Overview

Described herein are systems and methods for psychoacoustic processing of audio materials. In the following description, for purposes of explanation, numerous examples and specific details are set forth in order to provide a thorough understanding of the aspects of the systems and methods. It will be evident, however, to one skilled in the art that the present invention as defined by the claims may include some or all of the features in these examples alone or in combination with other features described below, and may further include modifications and equivalents of the features and concepts described herein.

II. Example Embodiment: Rezonyx System

Figure 1:
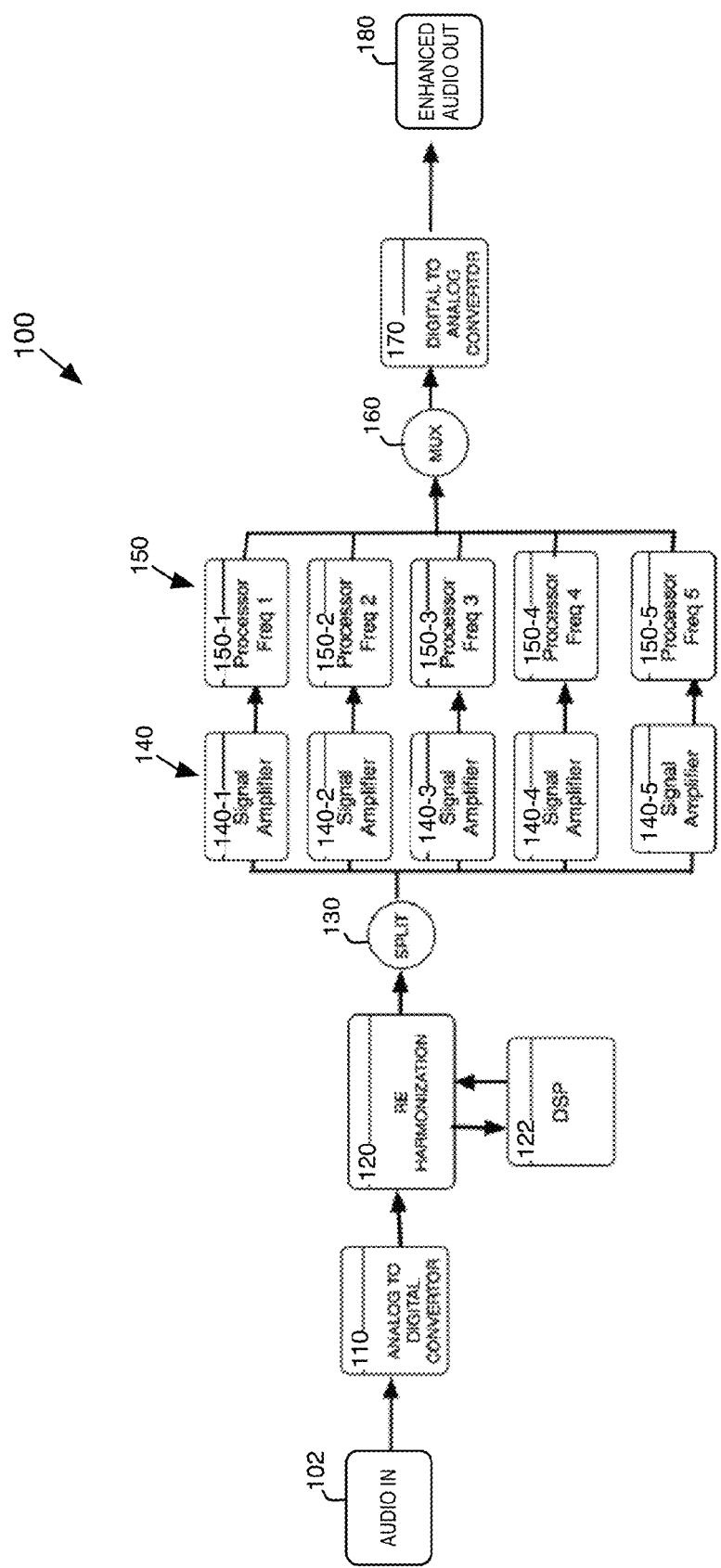
FIG. 1 is a schematic block diagram of a system for enhancing audio material in accordance with an example embodiment.

Referring to FIG. 1, in some embodiments, a Rezonyx system 100 for processing an input sound 102 to an enhanced output sound 180, may include an input transducer 110 (which may also be referred to as an "input converter", "analog to digital converter", or "A/D converter") for converting the input sound 102 to an electric input signal, and an output transducer 170 (which may also be referred to as an "output converter", "digital to analog converter", or "D/A converter") for converting a processed electric output signal to an output sound 180. In some embodiments, a forward path may be defined between the A/D converter 110 and the D/A converter 170, and may include a reharmonizer 120 and signal processing unit 122, a splitter 130 and an amplifier module 140 followed by a processor module 150. In some embodiments, amplifier module 140 and processor 150 may be collectively referred to as a Rezonyx processor.

In some embodiments, reharmonizer 120 may retune or reharmonize the input signal to a new base frequency (e.g., adjusted from the standard base frequency where note A has a frequency of 440 Hz, also sometimes referred to as A440). In some embodiments, splitter 130 may split or sample the harmonized (or in some embodiments, unharmonized) audio material into a number of desired stages, or frequency bands. Amplifier module 140 may include one or more parallel signal amplifiers 140-1, 140-2, 140-3, 140-4, 140-5, each configure to amplify a stage of the audio material sampled by the splitter 130. The processor module 150, and/or each processing unit 150-1, 150-2, 150-3, 150-4, 150-5, may then filter and/or delay the amplified input signal of one or more of the stages to a preset spectral frequency band, e.g., selected by input data. In some embodiments, a separate processor may be used for each frequency processed as shown in FIG. 1, but the system 100 could utilize the power of a single DSP, e.g., if the architecture is be optimized so no latency occurs in the processed signal.

After Rezonyx processing and retuning of one or more of the signal bands or stages, a signal mux interface 160 may downmix or multiplex all of the parallel signals, e.g., with an LG-estimator unit for estimating loop gain in each frequency band. In some embodiments, the muxer 160 may provide the enhanced material to the digital to analog convertor 170, which is then delivered back as an enhanced audio stream 180. In some embodiments, the mux 160 and/or other modules may be used to overlay one or more processed frequency bands onto the audio material to create enhanced audio material.

In some embodiments, the enhanced audio stream 180 may be formatted as it was at input and therefore does not require a proprietary player to play the information back. All filters may be engaged or disengaged as desired through the process 100. Levels of filtered information can be directly controlled, for example, at the muxer 160.

In some embodiments, a Rezonyx retuning system such as system 100 may be used to process audio material by reharmonizing the base frequency of the material from the standard 400 Hz, for example, to achieve desired frequencies for one or more notes to optimize the psychoacoustic properties of the material. Table 1 below, for example, shows a number of music notes retuned to their optimal psychoacoustic frequencies. The far right column described the tuning shift in cents from standard a 440 Hz tuning (i.e., where the "A" note is tuned to 440 Hz) to achieve the desired frequency for each note. See also section III below for an overview of properties and potential benefits of such desired frequencies in accordance with psychoacoustic principles. One skilled in the art will appreciate that Table 1 represents shifts to example frequencies within one octave. Notes within other octaves may undergo similar shifts using the principles shown and described herein.

TABLE 1

Music Notes with Harmonic Frequencies and Tuning Shift

| Desired Frequency/Note | Corresponding Frequency of Retuned "A" Note | Shift from Standard A440 Hz (in cents) |
| --- | --- | --- |
| 174 Hz = F3 | 438.48 Hz | −06 cents |
| 285 Hz = C#4 | 452.37 Hz | +48 cents |
| 396 Hz = G4 | 444.34 Hz | +17 cents |
| 417 Hz = G#4 | 441.78 Hz | +7 cents |
| 528 Hz = C5 | 444 Hz | +16 cents |
| 639 Hz = D#5 | 451.84 Hz | +46 cents |
| 741 Hz = F#5 | 440.60 Hz | +2 cents |
| 852 Hz = G#5 | 451.33 Hz | +44 cents |
| 963 Hz = B5 | 428.96 Hz | −44 cents |

Figure 2:
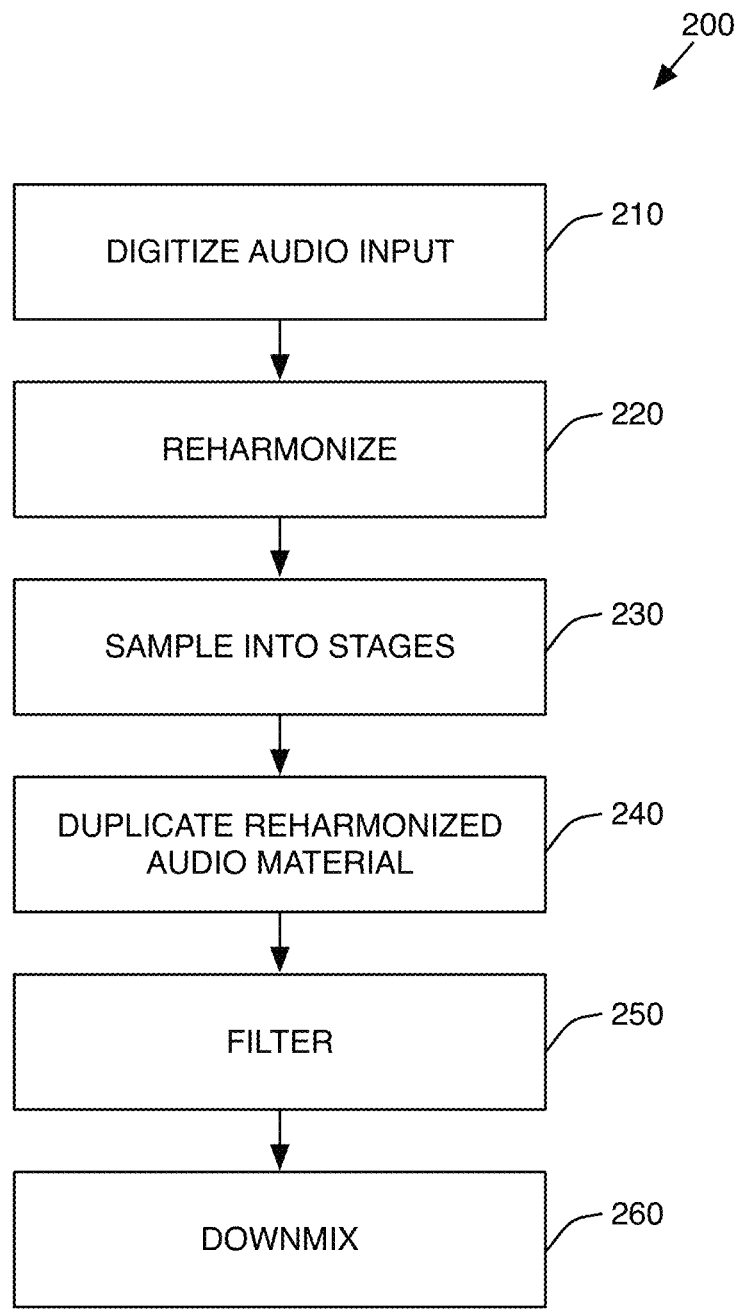
FIG. 2 is a flowchart of an example method of enhancing audio material in accordance with an example embodiment.

Turning now to FIG. 2, a flowchart illustrating a method 200 of using an exemplary Rezonyx system to for psychoacoustic processing of audio material may comprise a multi-stage process. For example, a first stage may involve digitizing 210 an audio input (e.g., using an analog to digital converter as described above with respect to FIG. 1) and reharmonizing 220 the audio material to a desired base frequency. For example, reharmonizing the base note by +16 cents may shift the base note from 440 Hz to 444 Hz, thereby shifting the corresponding C5 note to a desired frequency of 528 Hz.

Such reharmonization may be used to bring the audio source material into a tuning frequency that is proven to alter mind and body process. In all prerecorded music material there is almost always specific frequencies in which musical overtones occur resonances that relate to notes on the musical scale. Using today's A440 base tuning reference (i.e., A=440 Hz), the frequencies generated by notes on the musical scale may be out of alignment with our body. In contrast, reharmonizing or shifting the base note (and/or one or more other notes of the scale) may provide more natural tuning frequencies and an overall more enjoyable, moving, and effective listening experience.

In some embodiments, harmonization of the input signal 220 may be provided by software that instructs a digital signal processor to perform this transform. In some embodiments, such a process can be utilized within software of embedded in silicon for a variety of devices.

In some embodiments, a second stage process may be achieved by sampling in 230, duplicating the reharmonized audio material 240, and filtering the stages 250 to create a plurality of narrow frequency bands centered around the harmonic frequencies scientifically associated with ability to alter the body or brain process. The core frequencies chosen depend on the outcome the listener or organization requires. A list of frequencies and properties is detailed below, under the section titled "III: Frequency Band Principles". The frequencies may be selected within software, or may be set to preset buttons, or accessed via a menu or other interface on a hardware device.

These narrow frequency bands may be created using harmonic filters which sample the harmonized audio material in stages, duplicate the re harmonized material then filter out all frequencies not within the chosen band structure, for example using a high Q setting. A high Q setting provides a soundstage where the introduced frequencies are largely imperceptible to the human ear as hearing is comparatively insensitive to extremely narrow, high Q resonances, unlike broad, low Q resonances, which are very recognizable.

Once the stages of harmonized audio material are filtered to create the desired band structure, the material may be downmixed 260 or multiplexed to provide a reharmonized and enhanced audio output. In some embodiments, the downmixed material may be converted back to analog before outputting the enhanced audio output (e.g., as shown in FIG. 1.)

With audio material processed by Rezonyx the program material provides capabilities that can be altered during the stream or fixed for a desired result and the beginning of the stream. Rezonyx encoded audio or data provides the ability to create engagement, excitement, relaxation, and a number of other human based states. The Rezonyx process may happen at multiple points. For example, one such point is at point of engagement in the device, e.g., live processing the incoming audio material. In this method the process may be embedded into silicon or a media player, decoder or device with software. Another such point is where the program material (e.g., audio and/or video) may be encoded or finalized into the media file.

Figure 3:
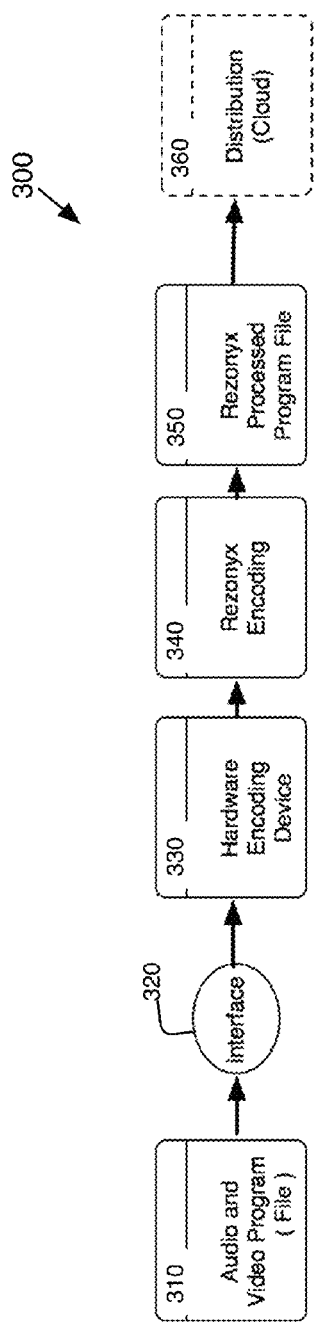
FIG. 3 is a schematic block diagram of a system and method for preprocessing and encoding audio and video program material in accordance with an example embodiment.

Turning now to FIG. 3, a schematic block diagram of an example system and method 300 for live processing of an audio and video program file 310 is shown. In this example, the file 310 is input into an interface 320, e.g., through a port or API interface. A hardware encoding device 330 may encode the file for manipulation by the hardware (e.g., digitization and/or format encoding as desired). A Rezonyx encoding module 340, e.g., implemented as a software module, hardware module, or a combination thereof, may be used to reharmonize, sample, filter and/or process the file to create the desired frequency/note characteristics, e.g., using a method 200 of FIG. 2 and or principles of system 100 of FIG. 1. In some embodiments, encoding module 340 comprises hardware and/or software instructions for shifting, retuning and/or filtering one or more stages or frequency bands in the audio material. In some embodiments, each retuned frequency corresponds to a musical note, as shown in Table 1, for example, such that retuning one or more notes (referred to herein as "polyphonic retuning") adjusts and filters the frequency of multiple notes in the original audio material. After such processing and downmixing or multiplexing of the various stages or bands, the resulting Rezonyx processed program file 350 may then be stored and/or distributed 360 to users, e.g., via a network.

Figure 4:
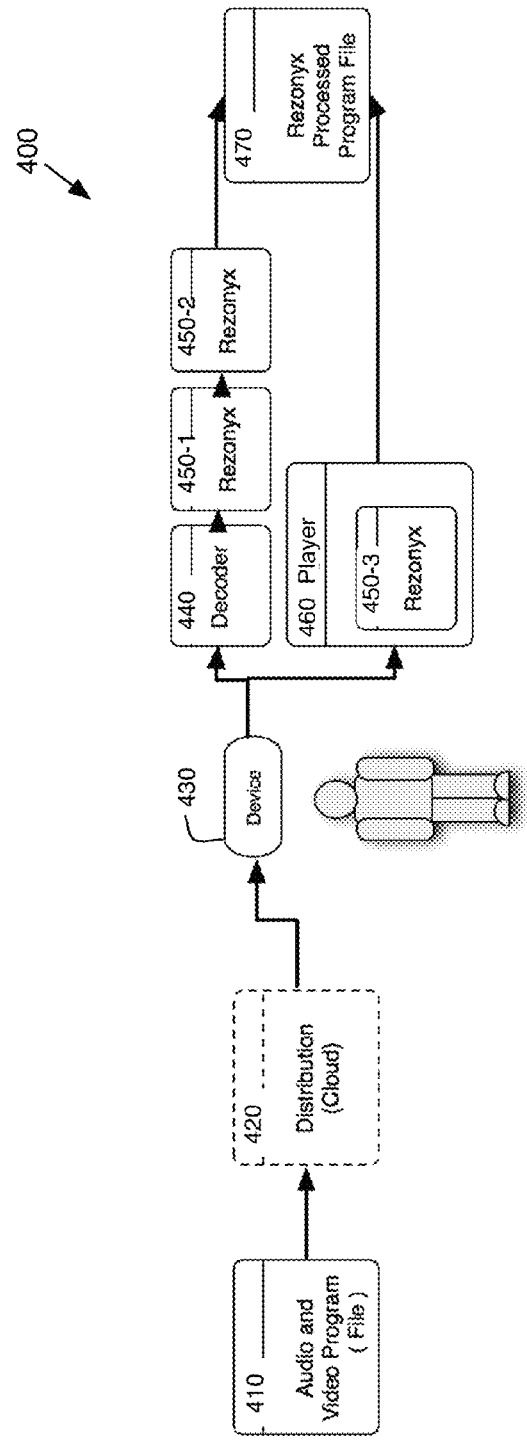
FIG. 4 is a schematic block diagram of a system and method for live processing of an audio and video program file in accordance with an example embodiment.

Referring to FIG. 4, a schematic block diagram is used to illustrate an example system 400 and method for preprocessing and encoding audio and video program material in accordance with an example embodiment. In this example, a stored or pre-recorded audio and/or video program file 410, or data, may be sent or distributed, e.g., over a network or distribution cloud 420, to a Rezonyx processing device 430. In some embodiments, the device may include one or more decoders 440 and/or Rezonyx processing modules 450-1, 450-2 and/or 450-3, e.g., to retune one or more frequencies of the material in accordance with the psychoacoustic principles and methods described herein. In some embodiments, the device 430 may include a player 460 to provide output of one or more portions of the processed data, e.g., to provide an output of particular notes, stages or samples during processing, and/or to play Rezonyx-processed material in "real-time" (e.g., as it is processed). In some embodiments, Rezonyx-processed program files 470 are output from the system 400, and may be stored, transmitted, and/or played by a user as desired.

II. Example: Polyphonic Rezonyx Tuning

In some embodiments, a method of retuning an instrument involves shifting or retuning a combination of frequencies, where each frequency corresponds to a musical note. For example, rather than retuning the base frequency to achieve a desired frequency shift of a particular note in a selection of audio material, each frequency relating a musical note in the audio signal may be transformed by shifting its frequency, e.g., by the amount shown in Table 1 above. Is such embodiments, each note, and therefore each frequency relating to that note, may be shifted or transformed so it resonates with the physiology of the human body (e.g., in accordance with the principles or characteristics described below in section III).

As a musical scale over 1 octave comprises of 12 notes (C, C#, D, D#, E, F, F#, G, G#, A, A#, B) each of these notes has a corresponding frequency over 1 octave, and therefore over 3 octaves there are 36 notes and frequencies.

Figure 5:
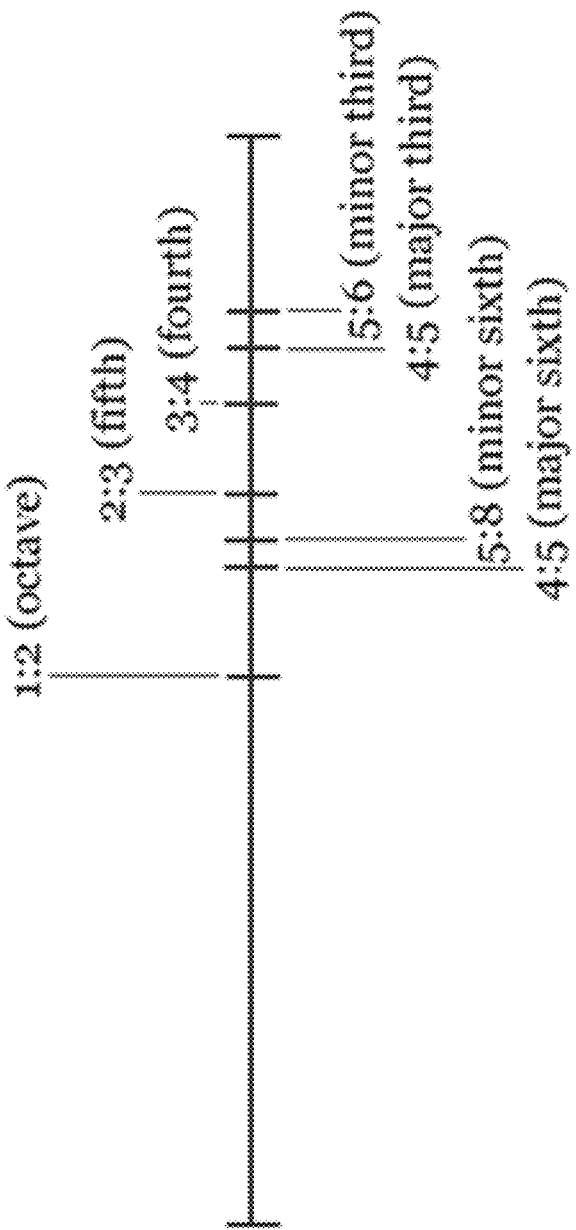
FIG. 5 is a schematic illustration showing the mathematical harmonic division of strings, as used in music today.

The ability to harmonically retune or shift one or a plurality of these notes so they are in tune with human physiology provides a polyphonic retuning system where music is tuned to the human body, as opposed to a mathematical algorithm where each note is divisible by math— e.g., in accordance with standard harmonic divisions as shown in FIG. 5.

As discussed above, Table 1 above provides a list of musical notes and corresponding frequencies and the representative amount of transforming, or retuning, to take place to achieve the example desired frequency for each note (as listed in the left hand column). The shift in cents (right hand column of Table 1) describes the amount of harmonic retuning to take place for each note within the example octave. In some embodiments, a plurality of these notes are utilized and retuned together, thereby providing for polyphonic shifting of notes, e.g., from Pythagorean or equal temperament scaling to a physiological harmonic tuning as a base for the Rezonyx system, e.g. using the system 100 of FIG. 1 and/or method 200 of FIG. 2. In some embodiments, such multi-note retuning may be performed live (e.g., as shown and described above with reference to FIG. 3) or post-processed on stored audio material (e.g., as shown and described above with reference to FIG. 4).

Figure 6:
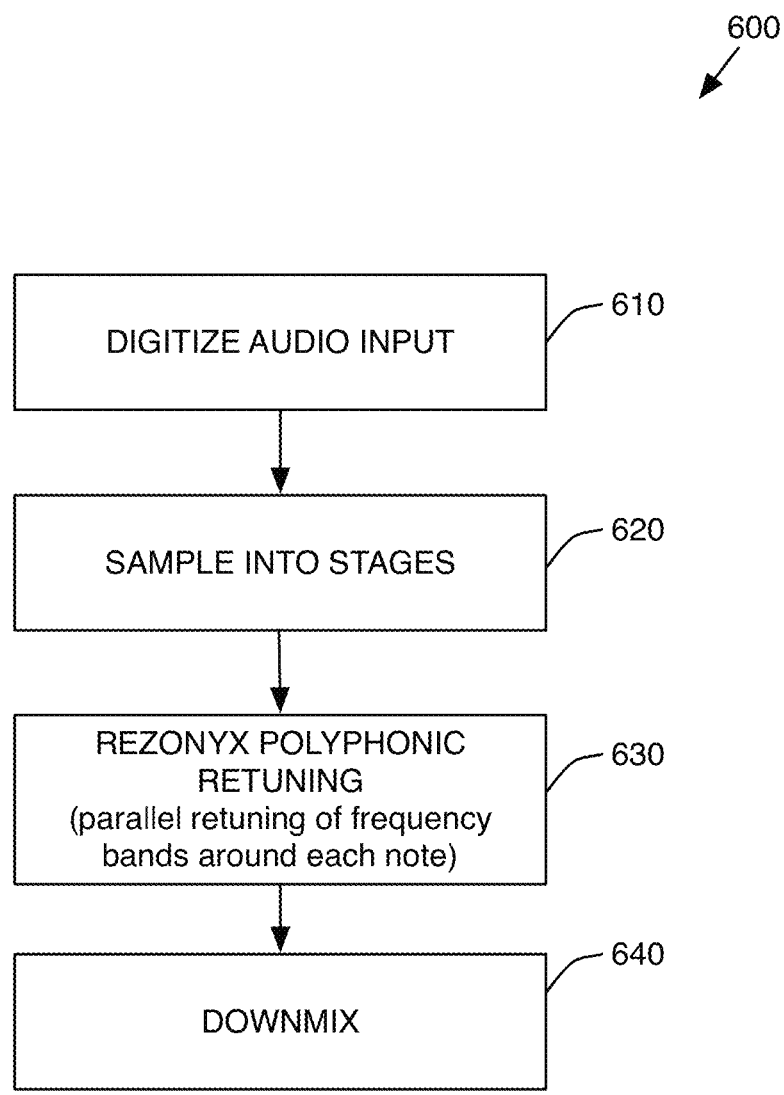
FIG. 6 is a flow chart of a method of polyphonic tuning involving shifting of frequencies related to each note in a musical piece, in accordance with an example embodiment.

Referring to FIG. 6, in some embodiments, an example Rezonyx method 600 may be a system whereby musical instruments can be tuned to the specific Rezonyx selected frequencies (e.g., frequencies from Table 1 above) relating to musical notes in the musical scale. For example, such a method 600 may include digitizing an audio input 610, e.g., using an A/D converter 110 as shown in FIG. 1. The digitized signal may then be sampled 620 into stages for processing, e.g., using a splitter 130 of FIG. 1. In some embodiments, the signal may be reharmonized or retuned to a new base frequency before splitting as described above. In some embodiments, such reharmonizing step may not be used.

Following splitting of the signal into desired frequency bands, e.g., each band corresponding to a musical note in the spectrum of notes used in the audio material, each band may be tuned and/or filtered, e.g., as described above with respect to FIGS. 1 and 2, to provide an optimal retuned frequency for each note. Such "polyphonic retuning" 630 of the stages of material may be performed in parallel, for example, using Rezonyx amplifiers 140 and processors 150 as shown and described herein. Once all notes are retuned, the audio material may be multiplexed, or downmixed, e.g., using a mux 160 of system 100.

In some embodiments, such a polyphonic retuning method may be applied to keyboards and other fretless instruments. In some embodiments fretted instruments such as guitars, bass, etc. may require or be fitted with a new fretting system for each string. In some embodiments, fretless instruments would be able to tune to these frequencies and fingers could play the notes without frets.

In some embodiments, a purpose of a Rezonyx tuning system using the frequencies shown in Table 1, or other desired frequencies and/or frequency shifts, may be to ensure that every note (or at least one or more notes, in some embodiments) in the musical scale resonates with the human body. In such embodiments a step in the Rezonyx process may be to recalibrate every note in the musical scale to a frequency that is resonant with the human physiology.

For example, nearly all music today is tuned using a modern standard of 12-tone temperament scaling and A 440 base reference. Such tuning is perceived by our ear as sound and music but may not provide optimal resonance with aspects of our human physiology. Such suboptimal resonance characteristics may be analogous to a radio signal with a lot of static. By recalibrating the frequencies of sound using systems and methods described herein, notes within the music and other audio material may resonate better with the human physiology, e.g., analogous to improving clarity of a radio signal.

The ability to put forward a new process of tuning for all instruments may provide musicians and artists with a new way to create music that provides a more engaging experience.

III. Frequency Band Principles

Master frequency of 1122 Hz

UT—396 Hz—Intent: turning grief into joy, liberating guilt & fear

This frequency liberates the energy and has beneficial effects on feelings of guilt. It cleanses the feeling of guilt, which often represents one of the basic obstacles to realization, enabling achievement of goals in the most direct way. The 'Ut' tone releases you from the feeling of guilt and fear by bringing down the defense mechanisms. 396 Hz frequency searches out hidden blockages, subconscious negative beliefs, and ideas that have led to your present situations.

RE—417 Hz—Intent: Undoing Situations and Facilitating Change

The next main tone from the Solfeggio scale produces energy to bring about change. This frequency cleanses traumatic experiences and clears destructive influences of past events. When speaking of cellular processes, tone 'Re' encourages the cell and its functions in an optimal way. 417 Hz frequency puts you in touch with an inexhaustible source of energy that allows you to change your life.

MI—528 Hz—Intent: Transformation and Miracles (DNA Repair)

Tone 'Mi' is used to return human DNA to its original, perfect state. This frequency brings transformation and miracles into your life. The process of DNA reparation is followed by beneficial effects—increased amount of life energy, clarity of mind, awareness, awakened or activated creativity, ecstatic states like deep inner peace, dance and celebration. Tone 'Mi' activates your imagination, intention and intuition to operate for your highest and best purpose.

FA—639 Hz—Intent: Re-Connecting and Balancing, Relationships

Another frequency from the sacred Solfeggio scale. It enables creation of harmonious community and harmonious interpersonal relationships. Tone 'Fa' can be used for dealing with relationships problems—those in family, between partners, friends or social problems. When talking about cellular processes, 639 Hz frequency can be used to encourage the cell to communicate with its environment. This ancient Solfeggio frequency enhances communication, understanding, tolerance and love.

SOL—741—Hz Intent: Solving Problems, Expressions/Solutions

It cleans the cell ("Solve polluti") from the toxins. Frequent use of 741 Hz leads to a healthier, simpler life, and also to changes in diet towards foods that are not poisoned by various kinds of toxins. Tone 'Sol' cleans the cell from different kinds of electromagnetic radiations. Another application of this sound frequency is solving problems of any nature. The fifth frequency of the Solfeggio scale will also lead you into the power of self-expression, which results in a pure and stable life.

LA—852 Hz—Intent: Awakening Intuition, Returning to Spiritual Order

Tone 'La' is linked to your ability to see through the illusions of your life, such as hidden agendas of people, places and things. This frequency can be used as means for opening a person up for communication with the all-embracing Spirit. It raises awareness and lets you return to spiritual order. Regarding cellular processes, 852 Hz enables the cell to transform itself into a system of higher level.

Additional research conducted by Dr. Leonard Horowitz claims to have revealed three more Solfeggio frequencies:

SI—963—Hz Awakening

This tone awakens any system to its original, perfect state. It is connected with the Light and all-embracing Spirit, and enables direct experience, the return to Oneness. This frequency reconnects you with the Spirit, or the non-vibrational energies of the spiritual world. It will enable you to experience Oneness—our true nature.

174 Hz

The lowest of the tones appears to be a natural anesthetic. It tends to reduce pain physically and energetically. The 174 Hz frequency gives your organs a sense of security, safety and love, encouraging them to do their best.

285 Hz

This frequency helps return tissue into its original form. The 285 Hz frequency influences energy fields, sending them a message to restructure damaged organs. It also leaves your body rejuvenated and energized.

The tones are: 396, 417, 528, 639, 741 & 852. Following the pattern established by these original tones, additional frequencies can be calculated. There are three frequencies which can be calculated below the 396 before breaking the pattern (63, 174, 285) and there are infinite frequencies that can be calculated above the 852. See below:

63
174—reduce pain
285—influence energy fields
396—turn grief into joy
417—facilitate change
528—transformation & miracles
639—reconnecting, relationships
741—expressions/solutions
852—return to spiritual order
963—awaken perfect state
1074
1185

IV. Brain Wave Principles

3rd Stage Brain Wave Entrainment

There are four recognized brain wave ranges: Beta (14-30 Hz) is present in normal waking consciousness; Alpha (7-14 Hz) in states of relaxation; Theta (4-7 Hz) in meditative states; and the slowest, Delta (0.5-4 Hz) in deep sleep and profound meditative states. The most recently researched brain frequency is Gamma, which is the fastest, about 30.0 Hz and higher. Stage 3 finalizes the processing of psychoacoustic cues by incorporating Binarual beats into the source material.

Binaural beats, or binaural tones, are auditory processing artifacts, or apparent sounds, caused by specific physical stimuli. This effect was discovered in 1839 by Heinrich Wilhelm Dove and earned greater public awareness in the late 20th century based on claims coming from the alternative medicine community that binaural beats could help induce relaxation, meditation, creativity and other desirable mental states. The effect on the brainwaves depends on the difference in frequencies of each tone: for example, if 300 Hz was played in one ear and 310 in the other, then the binaural beat would have a frequency of 10 Hz.

Five Categories of Brainwaves

Category 1: Beta Brainwaves (14 to 32 Hz Alert, Focused)

Beta is the most common brain wave pattern: Beta brainwaves are produced when we are wide awake, alert, active and engaged in mental activity, usually involving more the rational, reality-oriented left hemisphere of our brain. When beta wave activity becomes very intense, our brain hemispheres become less synchronized. Beta state is required to function properly in your everyday life.

Features and Benefits of a Beta State

This is the brainwave for the fight-flight response

Increased concentration and alertness

Improved logic, reasoning and critical thinking

Feelings of anxiety, stress, scattered unfocused thought

NOTE: Excessive Beta brainwaves are also a feature of insomnia

Category 2: Alpha Brainwaves (7 to 14 Hz Relaxed Yet Aware, Meditative)

These are lower frequency waves: The state is generated when our thoughts are really not concentrated and our minds wonder freely, or we are in a relaxed state such as meditating or daydreaming. We also experience Alpha Brainwaves when we are gently busy with routine tasks like pottering in the garden, taking a shower, putting on makeup, doing light housework. Alpha is considered to be the bridge between the conscious mind and the subconscious mind.

Features and Benefits of an Alpha State

Our brain hemispheres become naturally synchronized, or in-phase with each other.

Relaxed detached (absent-minded) awareness and daydreaming mind.

Enables us to remember our dreams and meditative states.

Link between conscious and subconscious mind, gateway to meditation.

Receptive to casual and auto-suggestions (hypnosis state)

Increased vividness benefits creative visualization and triggers imagination

Increased memory retention, concentration & focus for super learning

Health Benefits Include:

Reduced anxiety

Alleviates stress and depression

Reduces chronic pain

Reduction of high blood pressure

Increases athletic performance

Increased cerebral blood flow

Increased motivation, energy, and happiness

Category 3: Theta Brainwaves (3.5 to 7 Hz Deep Relaxation, Twilight State)

Theta brainwave states have been used in meditation for centuries: It is common for people to feel as if they are in a trance, where the mind feels as though it may have gone to sleep although it is conscious of what is happening around it. Theta induces a capacity for prolonged daydreaming, where a loss of time may be experienced.

Theta waves are also conducive to visualization and creativity and the mind in this very relaxed state is highly receptive to direct suggestion under hypnosis. As with Alpha, in Theta our brain hemispheres are synchronized and we experience whole brain functioning.

Features and Benefits of Theta Brainwaves

Increased sense of inner peace and emotional stability

Deep relaxation

Improved memory

Heightened intuition and inspiration

Calms the chatter of your mind

Increased psychic abilities and sense of spiritual connection

Health Benefits of Theta Brainwaves

Speed healing, improved physical healing

Sleep onset and better more restful sleep

Release beneficial hormones related to health and longevity

Reduce mental fatigue

Reduction of anxiety and stress

NOTE: Research has proven thirty minutes a day of Theta meditation can dramatically improve a person's overall health and well being. Theta meditation has also been known to result in a reduced need for sleep.

Category 4: Delta Brainwaves (0.1 to 3.5 Hz Deep Sleep)

This is the slowest band of waves that our brains produce and they occur when we are in deep, dreamless sleep. These waves are very beneficial for the body, which restores and heals itself when in this state. The delta state releases anti-aging hormones, including melatonin and DHEA. Human growth hormone (HGH) is another anti-aging hormone that is increased when delta brainwaves are occurring inside the brain, due to the stimulation of the pituitary gland. HGH maintains the skin, bone density, cartilage, and the joints in your body as well as speeds up the healing process of joint and cartilage injuries. HGH can also help heal physical pain.

In healthy amounts, delta brainwaves can also cause a person to have an advanced state of empathy, understanding, and compassion for others.

Delta is the place of deepest relaxation, deepest healing, deepest spiritual connection and deepest connection with the subconscious mind. It is considered to be the gateway to the unconscious mind and the collective unconscious, bringing access to the universal psyche or mind.

Category 5: Gamma Brainwaves (40 Hz or Higher: Zen Mind Mastery)

Gamma brainwave states are the most rapid in frequency. Gamma has long been considered the brainwave that is able to link and process information from all parts of the brain. It is the frequency that brings with it the ability to process large amounts of information in relatively small amounts of time. Think of generating more Gamma activity as getting a processor upgrade for your brain.

Unfortunately Gamma brainwaves have received the least attention and research, although more attention is currently being paid to them.

Having high amounts of Gamma Brainwave activity has been associated with:

Having high levels of intelligence

Being compassionate

Having high amounts of self-control

Having greater than average feelings of natural happiness.

Increased awareness through your five senses

Research has indicated at moments when bursts of precognition or high-level information processing occur, your brainwaves briefly reach the Gamma state.

Each of us can use brainwave entrainment to achieve a variety of results. You may want to target a specific brainwave frequency range to help you relax. On the other hand you may want to increase you creative energy, improve your memory, deepen your sleep or get better results when playing a sport.

VI. Examples Applications/Use Cases

Systems and methods described herein may be used in various applications in different industries. The following use cases are intended only to provide example embodiments and are not intended to be limiting. Various other embodiments and applications may be employed without departing from the scope of the invention(s) hereof.

Use Case 1—Advertising

Advertising is created with the hope of a consumer engaging with the message created in the advertising. In some embodiments, a Rezonyx process may be employed to improve this engagement over a piece of advertising. In some embodiments, processing of audio and video advertising material may be provided as a service to advertising agencies and brands via the use of software.

Every advertiser, agency or group that produces messaging to a group of potential consumers is relying on the impact of that messaging. Psychoacoustic processing of advertising messages, e.g., using the Rezonyx process as described above with respect to FIG. 1, may be used to introduce desired auditory cues within the message in order to make the messaging more effective to the viewer or customer.

In some embodiments, an example method of using Rezonyx in an advertising application may include:

Consumer watches TV, Film/Video or listens to a particular piece of audio via a channel, a channel who's material is supported by advertising Advertising is pre coded with Resonyx filtering (to advertisers specifications of intended result or emotion)

Consumer engages with advertising and spectral enhancement provides a more compelling result than engaging with the advertising without the Rezonyx process.

Use Case 2—Medical

Sound therapy has been around for many years. Sound and frequencies resonate with out body chemistry and contain information that has scientifically been proven to change our body and minds state.

Much research has also been undertaken in using Ultrasound and sonar (sound based-information) to perform different aspects of healing and communication.

The Rezonyx process is designed to utilize sound and specific spectral filters to achieve results to body and mental health.

In some embodiments, an example method of using Rezonyx in a medical application may include:

Patient selects a piece of pre coded audio material which is retuned to body anatomy and has specific spectral filters added Patient engages with the material over use of a receiving or playback device Patient is monitored for results Patient achieves results via sound therapy Use Case 3—Education All education systems using digital program material (audio and video) rely on the information being presented being retained in the students mind.

Rezonyx provides spectral filters and a process that enhances the retention levels of audio and video program material.

In some embodiments, an example method of using Rezonyx in an education application may include:

Student Starts Video Course

Course is precoded with Rezonyx Data on the audio stream specifically targeted at retention of knowledge Student finished course and has higher retention rates of material than the uncoded version of the audio or video program material Use Case 4—Wellness/Fitness Gymnasiums, fitness clubs, health spas, yoga and meditation centers rely on return customers, new memberships and customer satisfaction. Such clubs and gymnasiums commonly play music or other audio material to engage and stimulate their customers in achieving customer satisfaction.

In some embodiments, gymnasiums, fitness clubs, health spas, yoga and meditation centers using the invention ma enhance their music by feeding an audio stream through the Rezonyx system, e.g., using a hardware device or have the music prepared using software, either locally or via an online software-as-a-service. The music may be prepared using processes described herein, such that the harmonic material included is inline with the outcomes they are looking to achieve.

In some embodiments, Rezonyx provides the ability to provide spectral audio filters onto mainline commercial music in order to create a more engaging euphoric and exciting experience.

In some embodiments, an example method of using Rezonyx in a fitness or gym application may include:

Customer is on exercise bike or participating in a class listening to music

Music is precoded with Rezones

End of workout customer feels more engaged

Figure 7:
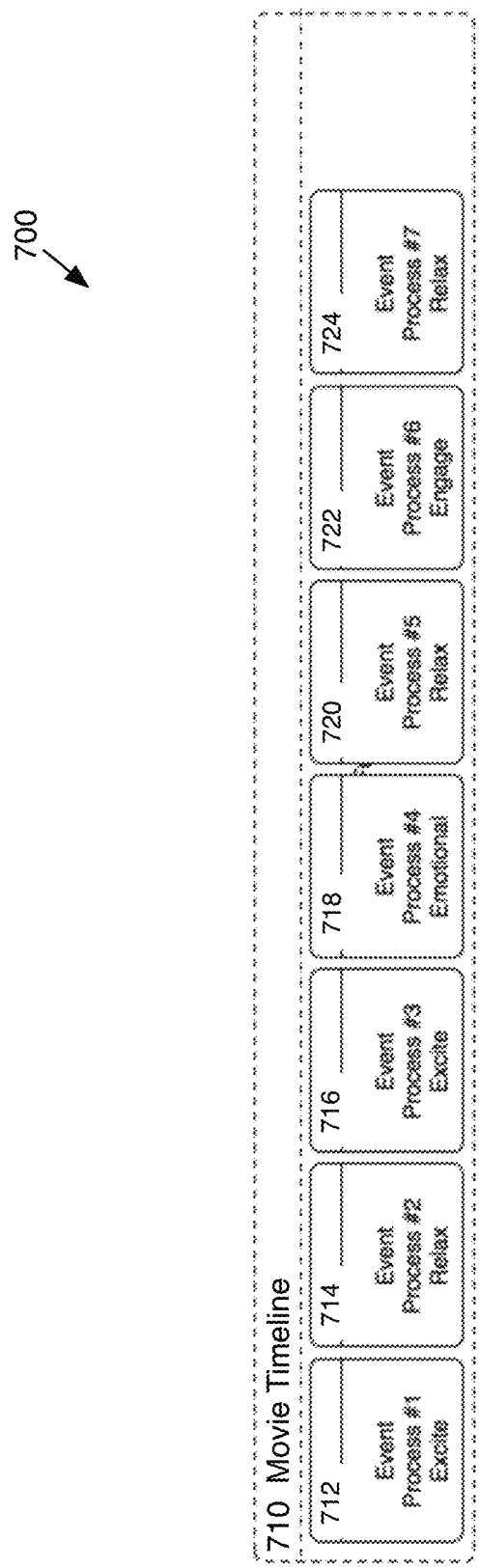
FIG. 7 is a schematic block diagram of a method for providing enhanced audio coding to an event structure in the timeline of a movie to enhance consumer response in accordance with an example embodiment.

Use Case 5—Film/TV (FIG. 7)

Movies are visual and auditory experiences that happen over time. In a movie, certain events are designed to create a human response. For example, special effects is one method of creating visual cues to emote a human response.

Similarly, Rezonyx methods described herein may be used to heighten the human response to events in a time-based sequence, for example as shown using a system or method 700 in FIG. 7. For example, in sample movie timeline 710, depending upon the storyline and score of the movie, it may be desirable to retune the audio steam at each event process to effect or enhance the mood of the moviegoer to correspond to the movie. For example, stages of the timeline and corresponding effects may include queues or desired emotions of excite 712, relax 714, excite 716, emotional 718, relax 720, engage 722, and relax 724. Of course, different emotions and/or responses may be encouraged depending upon the sequence of events in the movie storyline, images and/or score.

In some embodiments, such methods may be utilized to enhance moviegoers' experience and engagement, resulting increased box office revenues for studios.

In some embodiments, an example method of using Rezonyx in a motion picture film or television application may include:
   Studios provide sequence of events in a film timeline and attach emotions that are desired at the point of the event happening.
   Rezonyx provides the coding to the event structure in the timeline to enhance the consumer response.
   Consumer views movie and responds more favorably to the Rezonyx encoded audio than the unencoded data.
   Use Case 6—Music Musicians, music producers, composers and artists all create audio based content designed to engage an audience. The higher the engagement value, the more the perceived value of the content.

Rezonyx provides the ability for artists, music producers and composers to process their material using Rezonyx spectral cues. Cues may be selected and implemented depending upon the desired engagement result.

In some embodiments, an example method of using Rezonyx in a music production application may include:
   Artist creates song, and masters the song.
   Apply Rezonyx process to apply spectral cues.
   Distribute the song.
   Consumer listens to the song and has higher levels of engagement relative to unprocessed audio material.
   Use Case 7—Hearing Loss Rezonyx retuning systems and methods may be applicable for a user who has industrial deafness and has had his or her hearing analyzed, for example where the industrial deafness or any kind of deafness occurs in a selected range of frequencies where hearing is still active in specific frequencies.

In this example Rezonyx may retune the frequencies that are in the range where deafness occurs in a patient and shift the incoming frequencies of the input audio into a range where the patient's audio hearing is receptive. Such embodiments may allow for important information to still be processed and interpreted by the patient, albeit the original tuning of the input audio will be altered.

In some embodiments, another use may be to alter the gain or volume of any frequency range depending on the frequencies where hearing loss is diminished in this process.
   Use Case 8—Sports and Military Applications As described above a Rezonyx process may be used to increase the quality and performance of engagement of digital content. Such improved engagement may create neurological triggers and/or provide other benefits that enhance peak performance, excitement and relaxation.

In some embodiments, Rezonyx methods and systems described herein may apply to:
   Sporting arenas, to the theatre of war (e.g., areas where peak performance is highly valuable can be finely tuned individually for ultimate effectiveness);
   Healthcare industries where patients need to be in an optimum state for treatment;
   Entertainment industries including film, television, and advertising where an increase in the performance of engagement results in greater revenues.

In some embodiments, Rezonyx systems and methods may provide an auditory switch where the ability to enhance the effectiveness or engagement of a human being can be manipulated to affect a desired and/or probable outcome.

VII. Conclusion

The foregoing description illustrates various embodiments along with examples of how aspects of the systems may be implemented. The above examples and embodiments should not be deemed to be the only embodiments, and are presented to illustrate the flexibility and advantages of the systems and methods. In the figures, similar symbols typically identify similar components, unless context dictates otherwise. Other embodiments can be utilized, and other changes can be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

With respect to any or all of the sequence diagrams and flow charts in the figures and as discussed herein, each block and/or communication may represent a processing of information and/or a transmission of information in accordance with example embodiments. Alternative embodiments are included within the scope of these example embodiments. In these alternative embodiments, for example, functions described as blocks, transmissions, communications, requests, responses, and/or messages may be executed out of order from that shown or discussed, including substantially concurrent or in reverse order, depending on the functionality involved. Further, more or fewer blocks and/or functions may be used with any of the diagrams, scenarios, and flow charts discussed herein, and these diagrams, scenarios, and flow charts may be combined with one another, in part or in whole.

A block that represents a processing of information may correspond to circuitry that can be configured to perform the specific logical functions of a herein-described method or technique. Alternatively or additionally, a block that represents a processing of information may correspond to a module, a segment, or a portion of program code (including related data). Functional aspects described as modules need not be arranged or stored as a unit, and may include instructions, routines or program code distributed, stored and executed in any manner. The program code may include one or more instructions executable by a processor for implementing specific logical functions or actions in the method or technique. The program code and/or related data may be stored on any type of computer readable medium such as a storage device including a disk or hard drive or other storage medium.

The computer readable medium may also include non-transitory computer readable media such as computer-readable media that stores data for short periods of time like register memory, processor cache, and random access memory (RAM). The computer readable media may also include non-transitory computer readable media that stores program code and/or data for longer periods of time, such as secondary or persistent long term storage, like read only memory (ROM), optical or magnetic disks, compact-disc read only memory (CD-ROM), for example. The computer readable media may also be any other volatile or non-volatile storage systems. A computer readable medium may be considered a computer readable storage medium, for example, or a tangible storage device.

Moreover, a block that represents one or more information transmissions may correspond to information transmissions between software and/or hardware modules in the same physical device. However, other information transmissions may be between software modules and/or hardware modules in different physical devices.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

All citations and references, including without limitation references to web sites, are incorporated by reference herein in their entireties as if fully set out within the application.

What is claimed is:

1. A method of psychoacoustic processing of audio material, comprising:
   providing original audio material to be processed;
   sampling the original audio material into a plurality of stages;
   processing at least one of the plurality of stages to retune an original frequency of the at least one stage to a desired frequency; and
   downmixing the plurality of stages after said processing to create enhanced audio material.

2. The method of claim 1, further comprising reharmonizing the original audio material before said sampling to create reharmonized audio material.

3. The method of claim 2, wherein said reharmonizing comprises shifting an original base frequency of the original audio material to a new base frequency of the reharmonized audio material.

4. The method of claim 3, further comprising duplicating the original audio material.

5. The method of claim 4, wherein said processing further comprises filtering the at least one stage around the desired frequency.

6. The method of claim 5, wherein said downmixing further comprises overlaying the at least one stage on the original audio material.

7. The method of claim 3, wherein the original base frequency is 440 Hz and the new base frequency is any of 438.48 Hz, 452.37 Hz, 444.34 Hz, 441.78 Hz, 444 Hz, 451.84 Hz, 440.60 Hz, 451.33 Hz, or 428.96 Hz.

8. The method of claim 1, wherein said processing comprises shifting the original frequency of each stage of the plurality of stages to the desired frequency of each stage.

9. The method of claim 8, wherein said processing further comprises filtering each stage around the desired frequency of each stage.

10. The method of claim 9, wherein said processing further comprises amplifying each stage of the plurality of stages before said shifting.

11. The method of claim 9, wherein the desired frequency of each stage corresponds to a musical note.

12. The method of claim 11, wherein the desired frequency of each stage is any of 174 Hz, 285 Hz, 396 Hz, 417 Hz, 528 Hz, 639 Hz, 741 Hz, 852 Hz, or 963 Hz.

13. The method of claim 12, further comprising converting the original audio material to a digital signal before said sampling.

14. The method of claim 13, further comprising converting the enhanced audio material to an analog signal after said downmixing.

15. A system for psychoacoustic processing of audio material, comprising:
   a splitter for sampling an original audio material into a plurality of stages;
   a processor for processing at least one of the plurality of stages to retune an original frequency of the at least one stage to a desired frequency; and
   a mux for downmixing the plurality of stages after said processing to create enhanced audio material.

16. The system of claim 15, further comprising a reharmonization module for reharmonizing the original audio material before said sampling to create reharmonized audio material, wherein the reharmonizing comprises shifting an original base frequency of the original audio material to a new base frequency of the reharmonized audio material.

17. The system of claim 15, wherein said processor comprises a plurality of signal amplifiers and a plurality of corresponding frequency processors, wherein each signal amplifier and corresponding frequency processor is configured to process a stage of the plurality of stages of original audio material.

18. The system of claim 17, wherein the processor is configured to shift the original frequency of each stage of the plurality of stages to the desired frequency of each stage and to filter each stage around the desired frequency of each stage.

19. The system of claim 18, wherein the desired frequency of each stage is any of 174 Hz, 285 Hz, 396 Hz, 417 Hz, 528 Hz, 639 Hz, 741 Hz, 852 Hz, or 963 Hz.

20. The system of claim 15, further comprising an analog to digital converter for converting the original audio material from an analog signal to a digital signal.

* * * * *